US00PP19599P2

(12) United States Plant Patent
Maranto

(10) Patent No.: US PP19,599 P2
(45) Date of Patent: Dec. 30, 2008

(54) GRAPEVINE PLANT NAMED 'MARA SEEDLESS'

(50) Latin Name: *Vitis vinifera*
Varietal Denomination: cv. Mara Seedless

(75) Inventor: Joseph Maranto, Bakersfield, CA (US)

(73) Assignee: Anton Caratan & Son, Delano, CA (US)

( * ) Notice: Subject to any disclaimer, the term of this patent is extended or adjusted under 35 U.S.C. 154(b) by 0 days.

(21) Appl. No.: 11/976,684

(22) Filed: Oct. 26, 2007

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Buchanan Ingersoll & Rooney PC

(57) ABSTRACT

A new and distinct variety of grapevine is provided which abundantly forms attactive medium-to-large seedless berries having a rose-pink skin coloration in medium-to-large clusters. The fruit displays a sweet crisp flavor and is firm in texture. The fruit commonly is ready for harvest during October in the San Joaquin Valley of Central California, U.S.A., and displays good eating qualities as a table grape. The fruit firmness renders the fruit well amenable for handling, shipping, and storage.

1 Drawing Sheet

Figure 1:
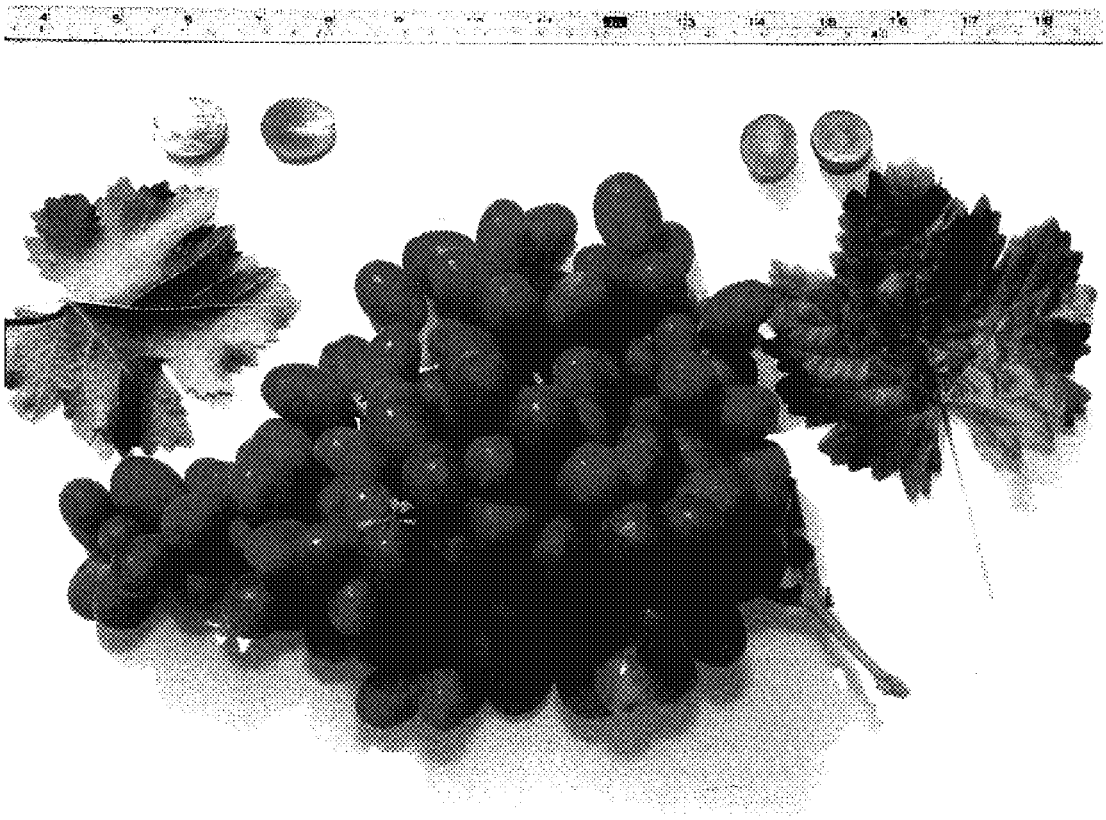

Botanical/commercial classification: *Vitis vinifera*/Grapevine.
Varietal denomination: cv. Mara Seedless.

Background of the New Variety

New grapevine varieties are being sought which display a combination of outstanding characteristics in areas such as vigor, productivity, and resistance to diseases and pests. Characteristics such as fruit size, coloration, flavor, taste, and seedless nature of the fruit, also are of importance when evaluating new varieties of grape plants.

The new variety of *Vitis vinifera* was created by artificial pollination during the course of a grapevine breeding program wherein two parents were crossed which previously had been studied in the hope that they would contribute the desired characteristics. Such breeding program was initiated during 1992 near Delano in the San Joaquin Valley of Central California, U.S.A. The cross that resulted in the creation of the new variety of the present invention was made in 1993. The female parent (i.e. the seed parent) of the new variety was the 'Red Globe' seeded grape variety (U.S. Plant Pat. No. 4,787). The male parent (i.e. the pollen parent) of the new variety was the 'Crimson' seedless grape variety (non-patented in the United States). The 'Crimson' male parent was released by the U.S.D.A. at Fresno, Calif. U.S.A., during 1989 and was formed by the cross of the 'Emperor' variety (non-patented in the United States) and an unreleased seedling named 'C33-1-99' (non-patented in the United States).

The parentage of the new variety can be summarized as follows:

'Red Globe'×'Crimson'.

The seeds resulting from the above pollination were sown and 210 small seedling plants were obtained which were physically and biologically different from each other. The resulting seedling plants were evaluated in detail and the new variety of the present invention was selected and was initially designated as R22-V188 and 'ACS V(26-30) R25R'.

It was found that the new grapevine of the present invention possesses the following combination of characteristics:

(a) forms attractive medium-to-large seedless berries having a rose-pink skin coloration in medium-to-large clusters which display a sweet crisp flavor, (b) commonly bears fruit during the month of October in the San Joaquin Valley of Central California, U.S.A., and (c) bears fruit that is firm and is well amenable for storage, handling, and shipping.

The new variety during observations to date has displayed no visible disease, and has displayed an ability to well resist cold, drought, heat and wind. The fruit of the new variety has been found to display excellent handling and shipping qualities combined with desirable dessert eating qualities.

The new variety of the present invention can be readily distinguished from its ancestors. More specifically, the 'Red Globe' parent forms large clusters of berries which possess seeds, and the 'Crimson' variety forms smaller berries which display lesser rose pink coloration which also is less uniform in its presentation.

The new variety of the present invention has been found to undergo asexual propagation beginning in 2000 near Delano in the San Joaquin Valley of Central California, U.S.A. by grafting on mature 'Thompson Seedless' rootstock (non-patented in the United States). Such asexual propagation has been conducted thereafter in successive years through 2006, and has shown that the characteristics of the new variety are strictly transmissible from one generation to another. Accordingly, the new variety undergoes asexual propagation in a true to type manner.

The new variety has been named 'Mara Seedless'.

BRIEF DESCRIPTION OF THE PHOTOGRAPH

The accompanying photograph shows as nearly true as it is reasonably possible to make in color illustration of this character typical specimens of the new variety. The photograph includes a typical cluster of the attractive grapes, upper and under surfaces of the leaves, and berries that are transversely and longitudinally sectioned in order to reveal the flesh which lacks seeds.

Dimensions in centimeters are shown at the top of the photograph for comparative purposes.

DETAILED DESCRIPTION

The chart used in the identification of colors is the Dictionary of Color by A. Maerz and M. Rea Paul (1930). Common color terms are to be accorded their ordinary dictionary significance. The description is based on the observation of plants growing on 'Thompson Seedless' rootstock outdoors near San Joaquin Valley of Central California, U.S.A.

Vine:

*Vigor.*—Exceeds that of its 'Red Globe' and 'Crimson' parental varieties.

*Productive capacity.*—Very productive.

*Trunk.*—Slender, includes long split strips, and six years after grafting the diameter commonly is approximately 2.4 inches (approximately 62 mm) measured 1 foot above the ground.

*Bark color.*—Brown (7-E-A), and Chicle Sarouk (7-E-8) underbark.

*Cane length.*—Medium, and commonly approximately 5 to 6 feet (approximately 1.5 to 1.8 m).

*Cane width.*—Medium, and commonly approximately 0.5 inch (approximately 13 mm) at node.

*Nodes.*—Generally round in configuration, and commonly spaced at a distance of 3 to 4 inches (approximately 76 to 102 mm).

*Shoot configuration.*—Substantially circular to slightly flattened, approximately 0.8 mm in diameter, and with longitudinal striations.

*Shoot color.*—Light green (30-D-3).

*Shoot texture.*—Smooth.

*Growing tip.*—Generally ascends straight up.

*Tendril length.*—Commonly approximately 4 to 6 inches (approximately 102 to 152 mm).

*Tendril form.*—Bifurcated and trifurcated.

*Tendril texture.*—Smooth.

*Bud shape.*—Pointed conical.

*Bud length.*—Commonly approximately 6 mm.

*Bud width.*—Commonly approximately 5 mm.

*Bud break.*—Commonly at the end of March or early April at the specified location.

Leaves:

*Size.*—Generally medium.

*Density.*—Heavy.

*Length.*—Approximately 4.5 inches (approximately 114 mm) on average for a mature leaf.

*Width.*—Approximately 4.7 inches (approximately 120 mm) on average for a mature leaf.

*Color.*—Green (23-J-11) Cossack green on the dorsal surface, and light green (22-G-5) on the ventral surface.

*Texture.*—Glabrous on the ventral surface.

*Petiole length.*—Commonly approximately 3.3 to 4.8 inches (approximately 84 to 123 mm).

*Petiole diameter.*—Commonly approximately 4 mm.

*Petiole sinus.*—U-shaped, and occasionally overlapping.

*Petiole color.*—Light green (23-L-1) Holly green.

*Lobe.*—Five-pointed.

*Color midrib.*—Grape green (21-K-7).

*Margins.*—Serrate with irregular teeth, commonly approximately 10 to 12 teeth per lobe, and approximately 50 to 60 teeth on entire leaf.

Flowers:

*Date of bloom.*—Early May at the specified location.

*Date of full bloom.*—Commonly third week of May at the specified location.

*Type.*—Fertile.

*Location.*—Primarily at the second or third node from the base on a spur.

*Petals.*—Five in number, and open from the bottom to the top.

*Sepals.*—Five in number, and commonly poorly developed.

*Stamen.*—Six in number, and upright and diverging.

*Pollen.*—Abundant, and yellow (9-L-4) Sunflower dandelion in coloration.

*Pistil.*—One in number, and produces a liquid to hold pollen to achieve germination.

*Filaments.*—Approximately 4 mm in length, and green (22-L-5) Cerro green in coloration.

Fruit:

*Time.*—Commonly ripe for commercial harvesting and shipment during early- to mid-October at the specified location.

*Berry size.*—Medium to large.

*Berry form.*—Uniform.

*Berry shape.*—Ellipsoidal elongated.

*Berry length.*—Commonly approximately 1.2 inches (approximately 30 mm).

*Berry width.*—Commonly approximately 0.7 inch (approximately 18 mm).

*Berry number.*—Commonly approximately 100 to 120 per cluster on average.

*Berry weight.*—Commonly approximately 6 grams on average.

*Cluster form.*—Commonly conical shouldered, and compact.

*Cluster size.*—Medium to large.

*Cluster length.*—Commonly approximately 8 to 10 inches (approximately 204 to 254 mm) on average.

*Cluster weight.*—Commonly approximately 500 to 700 grams on average.

*Solids.*—Approximately 18 percent sugar on Sep. 25, 2006.

*Acidity.*—Approximately 0.37 percent tritrable acidity.

*Sugar/acid ratio.*—Approximately 49.5.

*Juice pH.*—approximately 3.81.

*Seeds.*—Seedless, with an occasional few small traces of seeds.

*Capstem.*—Strong with long chalaza and attached to vascular tissue.

*Pedicel.*—Approximately 0.3 inch (approximately 7 mm) in length.

*Skin thickness.*—Relatively thick.

*Skin texture.*—Very firm.

*Skin cracking.*—No tendency to crack.

*Skin color.*—Rose pink (5-J-3).

*Lenticels.*—None visible.

*Flesh color.*—Light green (21-C-1).

*Flavor.*—Sweet and crisp.

*Eating quality.*—Good and meaty.

*Use.*—Dessert, table grape.

*Keeping quality.*—Very good, after one month in storage, still displays good appearance.

Development:

*Resistance to diseases.*—No disease problem has been observed.

*Resistance to cold.*—Good.

*Resistance to drought.*—Good.

*Resistance to heat.*—Good.

*Resistance to wind.*—Good.

*Shipping and handling.*—Excellent.

To further characterize the new 'Mara Seedless' variety DNA was extracted from dried leaf samples and DNA profiles were obtained at the Plant Identification Laboratory of the University of California, Davis, Calif., U.S.A., using base pairs for 10 standard microsatellite DNA markers. The data is presented hereafter. Those six markers indicated by an asterisk (*) have been adopted by the European Grape Genetic Resources Working Group and Foundation Plant Services as common markers to facilitate the exchange of data among grape research laboratories.

| Microsatellite DNA Marker | Allele Sizes in Base Pairs | |
|---|---|---|
| VVS2* | 135 | 151 |
| VVMD5* | 228 | 238 |

-continued

| Microsatellite DNA Marker | Allele Sizes in Base Pairs | |
|---|---|---|
| VVMD7* | 239 | 239 |
| VVMD27* | 181 | 194 |
| VrZAG62* | 189 | 189 |
| VrZAG79* | 247 | 259 |
| VVMD6 | 214 | 214 |
| VVMD28 | 247 | 261 |
| VVMD31 | 212 | 212 |
| VVMD32 | 253 | 273 |

The 'Mara Seedless' variety has not been observed under all possible environmental conditions to date. Accordingly, it is possible that the phenotypic expression may vary somewhat with changes in light intensity and duration, cultural practices, and other environmental conditions.

I claim:

1. A new distinct grape plant characterized by the following combination of characteristics:

(a) forms attractive medium-to-large seedless berries having a rose-pink skin coloration in medium-to-large clusters which display a sweet crisp flavor, (b) commonly bears fruit during the month of October in the San Joaquin Valley of Central California, U.S.A., and (c) bears fruit that is firm and is well amenable for storage, handling, and shipping;

substantially as herein shown and described.

* * * * *